US009316593B2

(12) United States Patent
Switkes et al.

(10) Patent No.: US 9,316,593 B2
(45) Date of Patent: Apr. 19, 2016

(54) RETROREFLECTORS FOR REMOTE DETECTION

(75) Inventors: Michael Switkes, Somerville, MA (US); Mordechai Rothschild, Newton, MA (US)

(73) Assignee: Massachusetts Institutes of Technology, Cambridge, MA (US)

(*) Notice: Subject to any disclaimer, the term of this patent is extended or adjusted under 35 U.S.C. 154(b) by 537 days.

(21) Appl. No.: 13/297,657

(22) Filed: Nov. 16, 2011

(65) Prior Publication Data

US 2012/0140224 A1 Jun. 7, 2012

Related U.S. Application Data

(60) Provisional application No. 61/414,810, filed on Nov. 17, 2010.

(51) Int. Cl.

*G01N 21/00* (2006.01)
*G01N 21/78* (2006.01)
*G01N 31/22* (2006.01)

(52) U.S. Cl.

CPC ................ *G01N 21/78* (2013.01); *G01N 31/22* (2013.01)

(58) Field of Classification Search

CPC ............ G02B 5/12–5/136; G02B 6/00; G01N 33/22–33/227; G02F 1/133553; B60Q 1/30–1/307; G01W 1/02; Y10S 977/92–977/922

USPC ........ 356/432; 422/82.05; 436/524; 359/533; 73/335; 161/2

See application file for complete search history.

(56) References Cited

U.S. PATENT DOCUMENTS

| | | | | |
|---|---|---|---|---|
| 3,830,682 | A * | 8/1974 | Rowland | 359/536 |
| 4,025,159 | A * | 5/1977 | McGrath | 359/514 |
| 4,150,570 | A | 4/1979 | Fuller | |

(Continued)

FOREIGN PATENT DOCUMENTS

| | | | |
|---|---|---|---|
| EP | 0 235 404 | A2 | 9/1987 |
| EP | 2 157 446 | A1 | 2/2010 |
| WO | WO 2012/078324 | A2 | 6/2012 |

OTHER PUBLICATIONS

International Search Report and Written Opinion in International Application No. PCT/US2011/060985, 17 pages, mailed May 31, 2012.

(Continued)

*Primary Examiner* — Abdullahi Nur
*Assistant Examiner* — Jamil Ahmed
(74) *Attorney, Agent, or Firm* — Hamilton, Brook, Smith & Reynolds, P.C.

(57) ABSTRACT

A detection system includes a retroreflector and a layer of material over the retroreflector, the material being subject to change in transmission with respect to an optical property of radiation, e.g. wavelength or polarization, with exposure to a phenomenon. The retroreflector and layer are illuminated from a radiation source of multiple aspects of the optical property. A sensor senses radiation retroreflected back through the layer. The retroreflector may, for example, be an array of or individual prisms or an array of or individual cat's eye microspheres. The layer of material above the retroreflector can include a colorimetric dye. In an embodiment, the retroreflector and layer are on the surface of a carrier that moves through a medium, e.g. a projectile or vehicle moving through the air. In a method of detecting a phenomenon, retroreflective elements are distributed in an array, as in the atmosphere or across a region of ground.

27 Claims, 11 Drawing Sheets

(56) References Cited

U.S. PATENT DOCUMENTS

| | | | | |
|---|---|---|---|---|
| 5,822,074 | A | 10/1998 | Deason et al. | |
| 6,507,441 | B1 * | 1/2003 | Eisenberg et al. | 359/627 |
| 6,668,104 | B1 | 12/2003 | Mueller-Fiedler et al. | |
| 7,262,856 | B2 | 8/2007 | Hobbs et al. | |
| 2006/0088946 | A1 | 4/2006 | Willson et al. | |
| 2007/0036680 | A1 | 2/2007 | Hobbs et al. | |
| 2007/0153343 | A1 | 7/2007 | Blyth et al. | |
| 2008/0199360 | A1 | 8/2008 | Shahriari | |
| 2009/0263071 | A1 * | 10/2009 | Stuck et al. | 385/12 |
| 2012/0105852 | A1 | 5/2012 | Patil et al. | |

OTHER PUBLICATIONS

Air Force Manual 10-2602 Nuclear, Biological, Chemical, and Conventional (NBCC) Defense Operations and Standards Review, United States Air Force (2003).

Bacsik, Z. et al., "FTIR spectroscopy of the atmosphere. I. Principles and Methods", *Applied Spectroscopy Reviews*, 39(3): 295-363 (2004).

Baker, Jr., A.A. "A History of Indicators", In *Chymia; annual studies in the history of chemistry*, 9: 147-167 (1964).

Costero, A.M. et al., Chromo-Fluorogenic Detection of Nerve-Agent Mimics Using Triggered Cyclization Reactions in Push-Pull Dyes, *Chemistry—An Asian Journal*, 5(7): 1573-1585 (Jul. 5, 2010).

Costero, A.M., et al., "Chromogenic detection of nerve agent mimics", *Chemical Communications*, 45: 6002-6004 (2008).

Field Manual No. 3-3, Fleet Marine Force Manual No. 11-17, Chemical and Biological Contamination Avoidance, United States Army (Nov. 16, 1992).

HPAC Hazard Prediction and Assessment Capability, Defense Threat Reduction Agency, Fort Belvoir, VA (1999).

Smart, J.K. "History of Chemical and Biological Detectors, Alarms, and Warning Systems", United States Army Soldier and Biological Chemical Command, Aberdeen, MD (2000).

Solladie-Cavallo, A., et al., "New aniline-containing amino alcohols from trans (R,R)-2- (2-nitropheny1)-3-phenyloxirane as useful intermediates for the synthesis of chiral ligands, bases, and benzoxazine nucleus",*J. Org. Chem*, 71(26): 9891-9894 (Nov. 26, 2006).

Switkes, Michael, et al., "Retroreflectors for remote readout of colorimetric sensors", *Sensors and Actuators B: Chemical*, 160: 1244-1249 (2011).

Younglove, T. and McCool, P.M. "Droplet size characterization of three aerial malathion spray programs", *Bulletin of Environmental Contamination and Toxicology*, 53: 493-500 (1994).

International Preliminary Report on Patentability from International Application No. PCT/US2011/060985, "Retroreflectors For Remote Detection," dated May 21, 2013.

* cited by examiner 1 2 3

A B C

RETROREFLECTORS FOR REMOTE DETECTION

RELATED APPLICATIONS

This application claims the benefit of U.S. Provisional Application No. 61/414,810, filed on Nov. 17, 2010.

The entire teachings of the above application are incorporated herein by reference.

GOVERNMENT SUPPORT

This invention was made with government support under Grant No. FA8721-05-C-0002 awarded by the U.S. Air Force. The government has certain rights in this invention.

BACKGROUND OF THE INVENTION

Colorimetric dyes are among the oldest chemical detection technologies, in use for at least 350 years and perhaps even since antiquity. See A. A. Baker, A History of Indicators, Chymia 9 (1964) 147-167. Sensors based on colorimetric detection are commercially available for a wide range of compounds and conditions. Because of their simple visual readout, detection systems based on colorimetric indicators can be very inexpensive and are thus widely deployed. For example, M8 and M9 colorimetric papers remain, over 45 years after their initial deployment, the most widely deployed detectors of chemical warfare agents (CWA) in the United States Military. See J. K. Smart, History of Chemical and Biological Detectors, Alarms, and Warning Systems, United States Army Soldier and Biological Chemical Command, Aberdeen, Md., 2000; Field Manual 3-3 Chemical and Biological Contamination Avoidance, United States Army, 1992.

The readout of colorimetric sensors is typically done by an operator in close proximity to the sensor who measures the color change by eye. In the case of detectors for hazardous materials, this presents difficulty for the operator who must physically enter the hazard zone. This requires personnel with special training, cumbersome personal protective equipment, and provision for decontamination upon return from the hazard zone. All of these preparations add up to turn an inexpensive and rapid sensor into a time consuming and expensive sensing system. Even if hazardous materials are not involved, reading out a large number of colorimetric sensors, for example to map the extent of contamination, is time consuming as the operator must physically approach each one. Proximity readout also presents problems for sensors in remote locations, for example monitoring water quality in remote lakes, where the difficulty of access renders visiting the sensors for readout impractical.

Discrete retroreflectors (i.e. not retroreflective tapes) have been used as part of a spectrometer for remote sensing of atmospheric vapors, transforming an otherwise bistatic measurement of the atmosphere into a monostatic one. See Z. Bacsik, J. Mink, and G. Keresztury, FTIR spectroscopy of the atmosphere. I. Principles and methods, Appl. Spectrosc. Rev. 39 (2004) 295-363. A sensor that uses optical changes in the path to a retroreflector is described in U.S. Pat. No. 6,668,104 to Mueller-Fiedler et al. A chemical sensor for remote interrogation having a surface relief structure, e.g., a surface grating, positioned over a retroreflector is disclosed in U.S. Pat. No. 7,262,856 to Hobbs et al. U.S. Pat. No. 5,822,074 to V. A. Deason et al. describes using a retroreflector that is partially isolated from the environment for remote readout of colorimetric detectors. There, a user must know where the isolated portion lies in order to compare that portion with the exposed portion. Unfortunately, this limits such a device to uses where the orientation of the retroreflector is known.

SUMMARY OF THE INVENTION

A detector for detecting exposure to any of a number of phenomena includes a retroreflector and a layer of material over the retroreflector, the material being subject to change in transmission with respect to an optical property of radiation with exposure to a phenomenon. The retroreflector and layer are illuminated from a radiation source of multiple aspects of the optical property, and a sensor senses radiation retroreflected back through the layer.

The sensor may be wavelength dependent. The retroreflector may, for example, include a prism or a cat's eye microsphere or an array of retroreflective elements, such as an array prisms or an array of cat's eye microspheres. In an embodiment, the material is subject to color change with exposure to the phenomenon and the radiation source is a source of radiation at multiple wavelengths. For remote detection, the light source preferably comprises at least two lasers of different wavelengths. For less remote detection, a non-collimated radiation source, even a flashlight of white light, may be used.

The radiation source and the detected wavelengths may be visible or non-visible. Sensors of more than two wavelengths may be used. For example, the sensor can include plural filters for different wavelengths. The layer above the retroreflector can include a colorimetric dye, for example an azobenzene dye that bleaches in the presence of organophosphates but does not bleach in the presence of common interferents.

The material may also be subject to change in polarization, optical chirality, or non-linear properties (e.g., variation in transmission with light intensity) with exposure to the phenomenon. In an embodiment, the material is subject to change in polarization and the radiation source is a source of radiation at multiple polarizations.

In some embodiments, the retroreflector and layer are on the surface of a carrier that moves through a medium or a region, such as a projectile, a ground vehicle, an airplane, an unmanned air vehicle (UAV), an unmanned ground vehicle (UGV), a submarine, or a person.

In a novel method of using the detector, detector elements are distributed in an array, as in the atmosphere or across a region of ground. The level of the detected phenomenon can then be mapped across the array. The retroreflective elements may be projectiles or attached to projectiles or other carriers and the response may be sampled as the projectiles or carriers move through the atmosphere or across the ground.

A method of detecting a phenomenon includes illuminating a retroreflector with radiation at multiple aspects of an optical property of the radiation through a layer of material over the retroreflector, the material being subject to change in transmission with respect to the optical property with exposure to the phenomenon. The method also includes sensing radiation retroreflected from the retroreflector.

The retroreflector, which can include a cat's eye microsphere or an array of prisms, may be illuminated with radiation at multiple wavelengths, e.g., with multiple lasers, and the material may be subject to color change. In an embodiment, the retroreflector is illuminated with white light and sensing radiation includes filtering at different retroreflected wavelengths. The retroreflector may be illuminated with radiation at different aspects of the optical property at different times.

The phenomenon to be sensed or detected by the devices and method described herein can include any combination of temperature, pH, and the presence or absence of a chemical.

A detection system includes an array of retroreflective elements distributed over a region, each retroreflective element having a change in optical characteristics with exposure to a phenomenon. Also included are a radiation source to illuminate the retroreflective elements and a sensor sensing radiation reflected from the retroreflective elements.

The change in optical characteristics can be any change in an optical property which affects transmission selectively, such as a change in color or change in polarization. The retroreflective elements may be projectiles or attached to carriers and may be distributed through the atmosphere or across a region of ground. Each of the distributed retroreflective elements can include one or more prisms or one or more cat's eye microspheres. The radiation source can include plural lasers of different wavelengths. Alternatively or in addition, the sensor can include plural filters for different wavelengths. In an embodiment, the retroreflective elements have a varied response in retroreflected wavelength with exposure to the phenomenon.

A method of detecting a phenomenon includes distributing an array of retroreflective elements over a region, each retroreflective element having a change in optical characteristics with exposure to the phenomenon; illuminating the array of retroreflective elements with radiation; and sensing radiation retroreflected from the retroreflective elements.

The retroreflective elements may be illuminated with white light and sensing radiation can include filtering at different retroreflected wavelengths. Alternatively or in addition, the retroreflective elements are illuminated with different wavelengths at different times. For example, lasers may be used to illuminate the array of retroreflective elements.

In one embodiment, a cat's eye retroreflector is coated with a layer of material that changes transmission with respect to an optical property of radiation when exposed to a phenomenon to be sensed.

The cat's eye retroreflector may be a projectile and may be a microsphere. The material can include a material that changes color with exposure to the phenomenon, such as a colorimetric dye.

A detection device includes a retroreflector and a layer of material over the retroreflector, the material being subject to change in transmission with respect to an optical property of radiation with exposure to a phenomenon.

Further, the detection device can include a radiation source of multiple aspects of the optical property to illuminate the retroreflector through the layer and a sensor sensing radiation reflected through the layer.

Although a wavelength dependent retroreflective element is preferred in this application, other technologies, such as presented in U.S. Pat. No. 5,822,074 (incorporated by reference in its entirety), may be used in the individual retroreflective elements of the array.

Detection systems and methods using wavelength dependent retroreflective elements according to embodiments of the invention offer advantages over other technologies. For example, in the '074 patent, differential readings are determined by exposing one region to the detected environment while protecting another; whereas, in the system disclosed here, differential readings are based on wavelength in viewing a single region. The present approach is suitable for detecting limited size drops, such as those from a pesticide that has been sprayed or any other aerosol. In contrast, devices that depend on differential readings from two regions of a retroreflector may not work because the droplets may not cover both regions. With the present wavelength dependent approach, measurements can be made independent of non-measured phenomenon such as dirt which affect both wavelengths the same, while dirt on only one region of the '074 patent device will affect the regions differently and thus affect the output. Further, it would be difficult to isolate the two regions of the '074 patent for phenomena such as temperature.

Another advantage of the present approach is that the orientation of the retroreflective device need not be known to detect exposure to a phenomenon, for example where the retroreflective device is not attached to a fixed support or where one or more retroreflective devices are thrown or dropped into the region to be measured. Further, unlike colorimetric surface structures, such as surface gratings, which reflect incident light in different directions to change color, the colorimetric layer or colorimetric dye described herein changes color by changing absorption of incident light. Advantageously, the colorimetric dye can be specific to a phenomenon to be measured, e.g., exhibiting a color change specific to the presence of organophosphates.

The ability to detect remotely presents significant advantages over currently available capabilities. As just one example, current US Air Force procedure for suspected chemical attacks is to deploy a grid of colorimetric M8 paper targets over the vulnerable area. After the attack, these targets must be read by airmen at relatively close range, tens of meters at most, subjecting them to contamination by the very chemicals they are attempting to detect. With the present approach, a retroreflective sensor can be read from a kilometer or more, or from an aircraft, well outside the range of potential contamination. In addition, the low cost of the sensor elements, and the modest cost of the illuminator/receiver, allows the dense deployment of sensors in applications which would not otherwise be economically feasible. With the present approach, retroreflective sensors can be deployed in large numbers to densely cover areas. In addition, such sensors may be used for remotely detecting low vapor pressure surface contaminants, a significant area of interest to the military.

Embodiments according to the present approach can be used to remotely monitor temperature. For example, a remote readout thermometer can include a retroreflector coated with a liquid crystal material that changes its polarization state in response to temperature.

Retroreflective elements and surfaces as described herein may also be used in standoff spectroscopy. On the retroreflectors' well defined and highly reflective surfaces, spectra measured in reflection may correlate with the large available library of absorbance spectra, allowing remote identification of unknowns on their surfaces.

A retroreflective detection system according to the present approach is described in a paper by Michael Switkes et al., "Retroreflectors for remote readout of colorimeteric sensors", *Sensors and Actuators B,* 160: 1244-1249 (2011), which is incorporated by reference in its entirety.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 13A illustrates remote interrogation from an aircraft. FIG. 13B illustrates ground-based remote interrogation.

DETAILED DESCRIPTION OF THE INVENTION

A description of example embodiments of the invention follows.

Figure 1A:
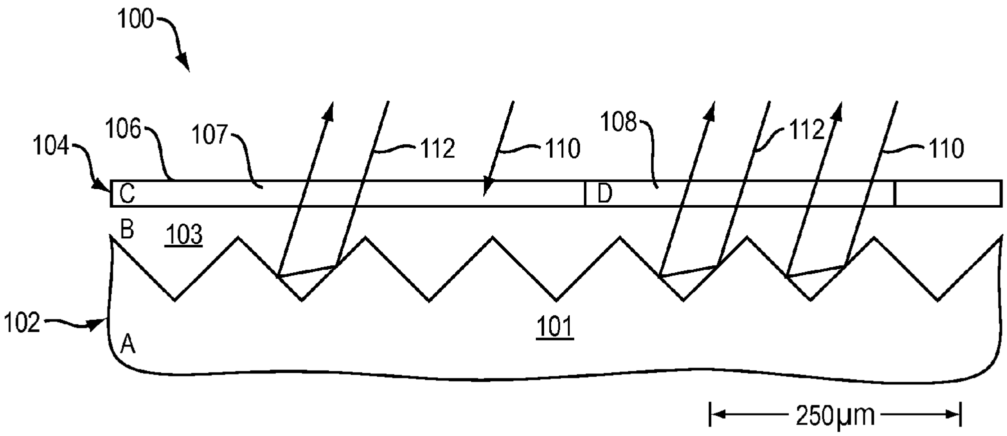
FIG. 1A illustrates one type of retroreflective device for remote detection according to an embodiment of the invention.

FIG. 1A illustrates a retroreflective device or sensing element 100 for remote detection according to an embodiment of the invention. Retroreflective device 100 includes a retroreflector 102 and a layer of material 104 over the retroreflector. The material is subject to change in transmission with respect to an optical property of radiation with exposure to a phenomenon. For example, layer 104 can be a semitransparent coating that changes its optical properties in response to an environmental stimulus. When the retroreflective element 100 is illuminated, the change in optical properties of layer 104 can be measured by an observer collocated with the illumination source, at distances and orientations which would not be possible without the retroreflector 102. The layer of material 104 can be colorimetric, i.e., the material can be subject to color change with exposure to a phenomenon. The material of layer 104 may also be subject to change in other intrinsic optical properties such as polarization, optical chirality, or non-linear properties, i.e., variation in transmission with light intensity. The retroreflector 102 and layer 104 of device 100 can be illuminated from a radiation source of multiple aspects of the optical property, as illustrated by beams 110 and 112 in FIG. 1A. Beam 110, which is transmitted through the layer of material 104 when the material is exposed to a phenomenon, differs from beam 112, for example, in wavelength, polarization, or light intensity. A sensor can be used to sense the radiation retroreflected back through the layer 104.

In an embodiment, device 100 includes a retroreflector, including a textured layer 101 and a clear protective overcoat 103, which is coated with a colorimetric layer 104 that includes a dye 106. In its native state 107, dye 106 absorbs one wavelength of light 110 and allows another wavelength of light 112 to pass. Dye 106, however, allows both wavelengths to pass when activated 108 by a phenomenon to be sensed, for example, when the dye is exposed to a chemical agent or to a change in temperature. Thus, when dye 106 is activated, retroreflector 102 reflects both wavelengths through colorimetric layer 104. Suitable dyes for dye 106 are described below.

The combination of colorimetric indicators with retroreflective substrates transforms what has been a proximity measurement using standard colorimetric sensors, into a measurement that can be performed at a distance. As their name indicates, retroreflective materials return light toward its source with high efficiency over a broad range of angles of incidence; unlike a mirror, there is no need for careful alignment of a retroreflector. Because retroreflectors are designed to reflect the light incident on them in the direction of the source rather than scattering or reflecting it away, their use increases the range at which optical changes can be detected. Retroreflective materials are commercially available and ubiquitous in road marking, vehicle conspicuity, and personnel visibility applications, among others. They are also remarkably inexpensive. Thus, deployment of large numbers of unpowered sensing elements is possible, opening up applications not feasible with expensive sensors.

Figure 1B:
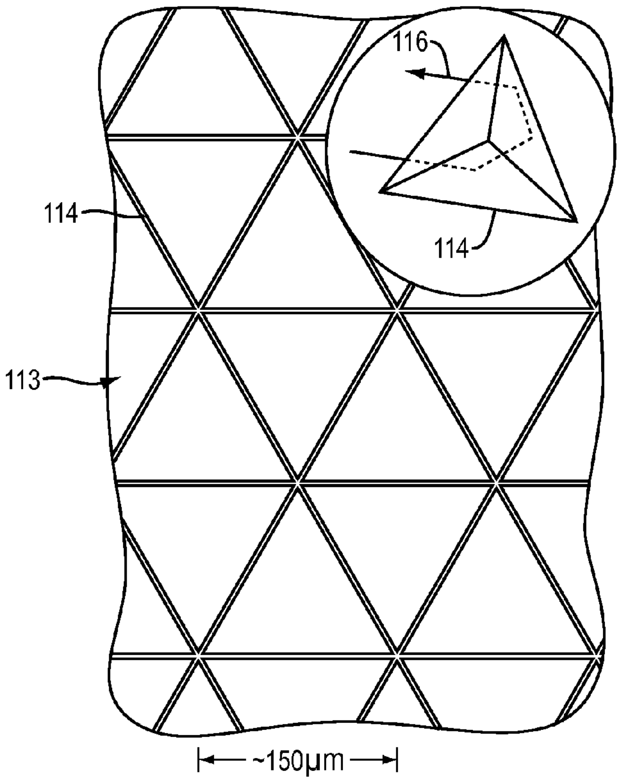
FIG. 1B is a top view of a retroreflective substrate that includes an array of prisms. The inset illustrates retroreflection in one of the prisms.

FIG. 1B shows a top view of a piece of retroreflective substrate 113 that includes an array of prisms 114. As shown, each prism 114 of the array can be triangular with a side length of about 150 μm. Adjacent retroreflective facets of prisms 114 may be oriented differently. The inset illustrates the reflection of light 116 incident on one of the prisms 114 in the direction of the source of the light. Substrate 113 or similar substrates, such as substrates that include an array of cat's eye microspheres (see FIG. 11), can be used to fabricate retroflective sensors described herein, including element 100 of FIG. 1A. As an example, a high performance class of commercially-available retroreflective materials includes ~100 μm-scale or larger corner cubes (microprisms) fabricated into a plastic tape. The tape can be covered with a protective layer of transparent plastic, leaving a physically robust flat surface. These substrates can be transformed into a remote sensor by coating them with a colorimetric dye in a polymer matrix. Due to the retroreflective surface, the color change can be observed with modest illumination at significant range. Preferably, the reflected light is measured at two or more wavelengths whose reflectivity is affected differently by the color change allowing other causes of reflectivity change (e.g. dust on the substrate) to be excluded. To measure at two or more wavelengths, the retroreflective device can be illuminated with white light and the retroreflected radiation sensed by filtering at different retroreflected wavelengths. Alternatively or in addition, the retroreflector can be illuminated with different wavelengths at different times.

Performance Analysis

Because the retroreflective material is highly efficient, even low-powered illumination allows readout at long distances. Using a simple model, one can predict the performance. The signal, i.e. number of photons returned to a single pixel of the receiver by the retroreflector $N_r$ is $$N_r = \frac{N_i}{A_i} A_{pixel} \Omega R_A [\varphi T_1 + (1 - \varphi) T_0] \quad (1)$$

$N_i$ is the number of photons emitted from the illuminating laser, $A_i$ the total area illuminated by the laser, $A_{pixel}$ the area of retroreflector imaged by a single detector pixel, Ω the solid angle of imaging aperture, $R_A$ the coefficient of retroreflection, ϕ the fraction of the pixel area which has changed color, and $T_0$ and $T_1$ the round-trip transmission in the unchanged and changed states of the colorimetric film, respectively. The aperture r of the imaging optic determines the solid angle; for ranges R>>r, $\Omega \approx \pi r^2/R^2$.

Figure 2:
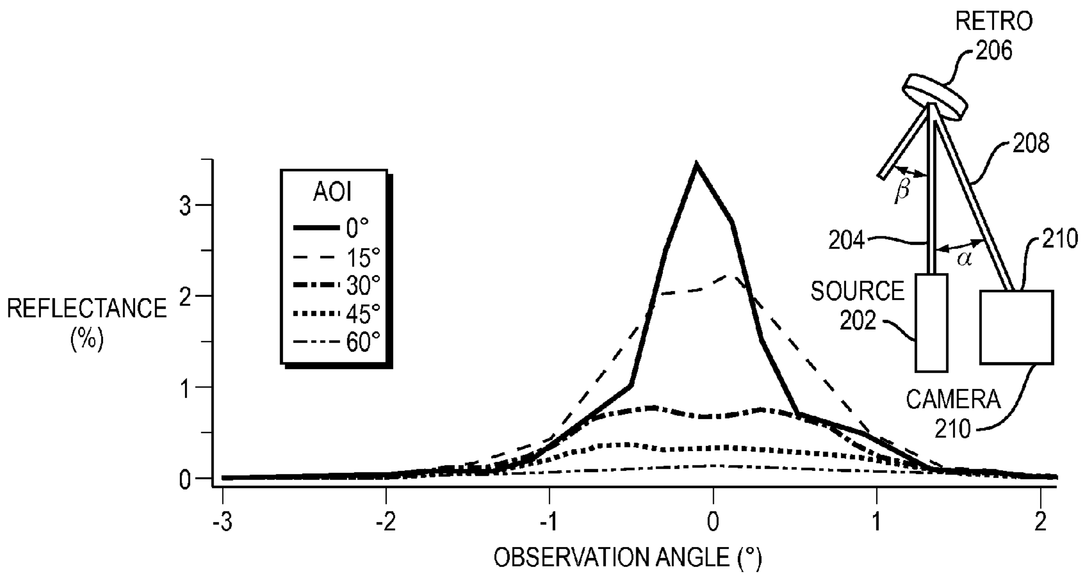
FIG. 2 illustrates exemplary results of the measurement of reflectance of a commercial retroreflector as a percentage of that of a properly aligned mirror. The reflectance is significantly lower than that of a mirror because reflections from adjacent retroreflector facets do not add coherently, along with local imperfections in retroreflector manufacture. However, the retroreflectance is significantly higher than the reflectance of a diffuse reflector, ~$2\times10^{-3}$%. The inset shows a diagram of the measurement apparatus. Angle alpha ($\alpha$) is the observation angle and angle beta ($\beta$) is the angle of incidence (AOI).

The coefficient of retroreflection $R_A$ is a measure of the efficiency of the retroreflector material. It is typically quoted by manufacturers in cd $lux^{-1}$ $M^{-2}$ which is dimensionally equivalent to $sr^{-1}$; typical values of $R_A$ for commercially available retroreflectors are in the range of 500-1000 $sr^{-1}$ whereas a perfectly diffuse reflector would have $R_A = 1/2\pi r = 0.16$ $sr^{-1}$. To confirm this performance, the return from a sample of commercially available retroreflector material (P-82, Reflexite Inc., New Britain, Conn.) at 660 nm was measured, along with the return of a mirror and a diffuse reflector (white Tyvek, DuPont, Wilmington, Del.). FIG. 2 illustrates results of the measurement of reflectance of the commercial retroreflector as a percentage of that of a properly aligned mirror. The reflectance is significantly lower than that of a mirror because reflections from adjacent retroreflector facets do not add coherently, along with local imperfections in retroreflector manufacture. The reflectance of a diffuse reflector is ~$2\times10^{-3}$%. A diagram of the measurement apparatus is shown in the inset of FIG. 2. The measurement apparatus includes a radiation source 202 to illuminate a target 206 (e.g., the retroreflector, the diffuse reflector, or the mirror) with an incident beam 204. A camera 210 measures the return or retroreflected beam 208. As illustrated, angle α is the observation angle and angle β is the angle of incidence (AOI). The retroreflected beam is at its maximum ~3% the intensity of a specular reflection from a properly aligned mirror, and ~1500× the intensity of a diffuse reflector. This corresponds to $R_A \approx 250$ $sr^{-1}$, slightly lower than the vendor-quoted value of 900 $sr^{-1}$. As shown below, this reflectance can be sufficient to enable remote readout at kilometer ranges and does not represent the limiting factor in system performance.

To detect changes in the dye color remotely while excluding other causes of changing light intensity, for example dirt on the surface of the retroreflector, the return at two wavelengths, and thus different values of $T_0$ and/or $T_1$, is compared. The ratio of photons returned at these two wavelengths, $N_r^{\lambda_1}/N_r^{\lambda_2}$ is then compared to a predetermined threshold value to declare the observation as a high-probability detection.

Since CWA, the primary target analytes, are generally encountered in small, concentrated droplets, the analysis here assumes a significant color change, $T_0/T_1 \approx 10$ over a small area on the surface of the sensor. In this case, the limit on the expected performance of a retroreflective detection system is the ability to detect sub-pixel (ϕ<1) changes in the dye layer. In other cases, particularly with dilute analytes, the limit could be the ability to distinguish the color change itself.

At 1 km, a 10 cm telescope has diffraction-limited resolution of ~5 mm. As an example, HPAC was used to calculate the distribution of expected droplet sizes for a chemical attack with a thickened VX-filled SCUD missile. See HPAC Hazard Prediction and Assessment Capability, Defense Threat Reduction Agency, Fort Belvoir, Va. 1999. The median drop diameter is ~1 mm, but near the edges of the contaminated area, where mapping might be most useful, droplets are significantly smaller, with an average of <0.5 mm. Malathion droplets sprayed in pest control efforts are smaller still with a mean size of ~275 μm. See T. Younglove, and P. M. McCool, Droplet size characterization of three aerial malathion spray programs, Bull. Environ. Contam. Toxicol. 53 (1994) 493-500. However, HPAC calculates the droplet size in air, whereas the colorimetric dye relies on interaction with a droplet on its surface. Therefore, ϕ depends on the size of color change on the surface of the retroreflector itself, and thus on the contact angle $\theta_c$ between the droplet and the retroreflector surface. The contaminated area ϕ can thus be increased by engineering a reduction in contact angle, causing the droplet to spread as much as possible on the retroreflector surface.

To quantify this, one can calculate the expected performance of a remote colorimetric retroreflector with a diffraction-limited imaging system. Assuming a 10 cm telescope and a commercially available scientific camera (EM11000, Princeton Instruments, Trenton, N.J.) with dark noise of ~4000 $e^-$/s, and a colorimetric dye with an on/off ratio $T_1/T_0=10$ at $\lambda_1$, fixing a false alarm rate of 1 in $2\times10^6$ gives a detection threshold of $N_r^{\lambda_1}/N_r^{\lambda_2}=8$. Allowing 3.5 s to measure each camera field at both wavelengths, and illuminating a 1 $m^2$ area with an eye-safe 5 mW laser, color change spots as small as 200 μm can be reliably detected from 100 m distance. Similarly, 2 mm spots can be reliably detected at 1 km.

Figure 3:
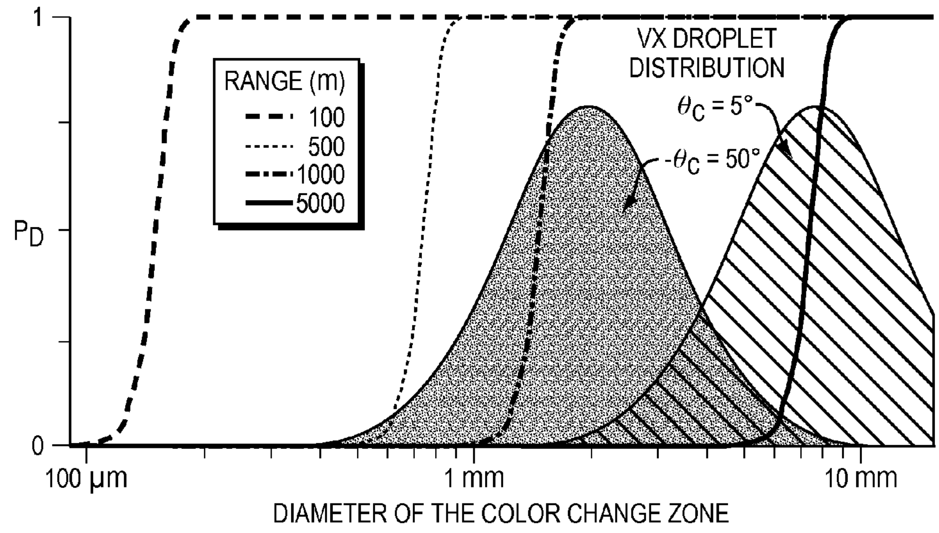
FIG. 3 illustrates calculated performance of a colorimetric retroreflector detection system as a function of the range and the size of the color change zone on the target. For comparison, the droplet distributions calculated for a VX missile attack are shown for two different contact angles, illustrating the potential importance of spreading on the retroreflector surface.

FIG. 3 shows the probability of exceeding this detection threshold, $P_D$, compared to the spot size distributions calculated for the VX attack discussed above for $\theta_c=50°$ and 5°, illustrating both the potential of the system to detect at range and the strong effect of surface wetting on performance. FIG. 3 illustrates calculated performance of a colorimetric retroreflector detection system as a function of the range and the size of the color change zone on the target. For comparison, the droplet distributions calculated for a VX missile attack are shown for the two different contact angles, illustrating the potential importance of spreading on the retroreflector surface. Note that the performance predicted in FIG. 3 may be optimistic, particularly at longer ranges, as the underlying calculations have assumed diffraction-limited imaging, and have neglected atmospheric effects.

Experimental Validation

Components of an embodiment of a retroreflective sensing system for the remote detection of organophosphate pesticides or nerve agents are described herein. In addition to a commercially available retroreflective tape (P-82, Reflexite, New Britain, Conn.), the exemplary sensor system includes a colorimetric dye, such as one of the custom synthesized colorimetric dyes described below, a polymer system for coating the dye onto the retroreflector, and an optical detection system for illuminating the retroreflectors and detecting the color change remotely.

Azobenzene Dyes

Figure 4:
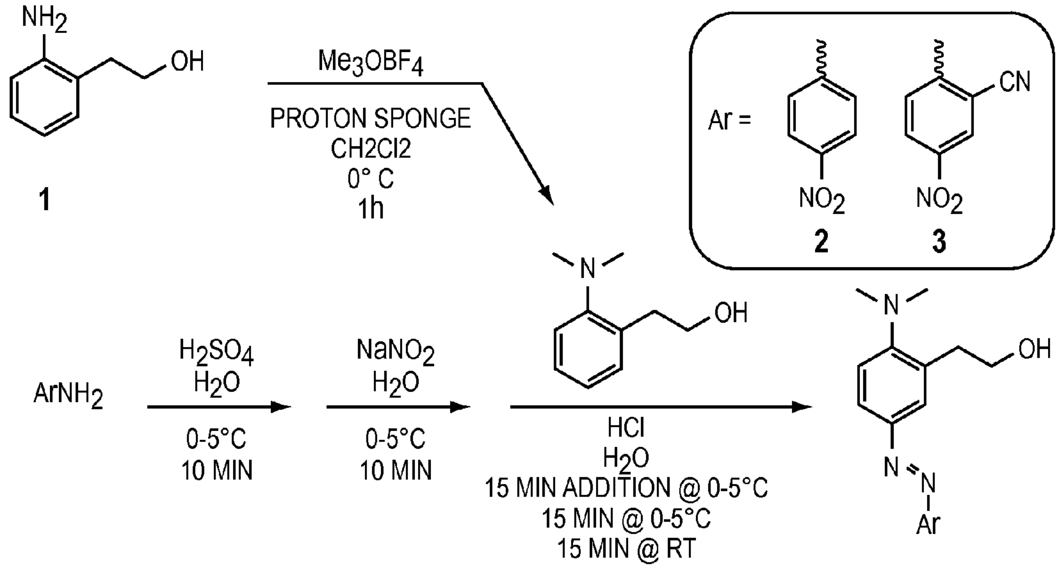
FIG. 4 illustrates the synthesis of exemplary organophosphate detecting azobenzene dyes that can be used in a colorimetric retroreflector detection system.

A set of colorimetric dyes that bleach in the presence of organophosphates but not in the presence of many common interferents were synthesized. This class of colorimetric dyes is based on a 2-(2-(dimethylamino)phenyl)ethanol structure that acts as a donor in a charge-transfer azo dye with a sufficiently electron-poor acceptor group. The first dye that was investigated was prepared by the method of Costero and co-workers who also investigated these materials for the colorimetric detection of nerve agent simulants. See A. M. Costero, S. Gil, M. Parra, P. M. Mancini, R. Martinez-Máñez, F. Sancenón, and S. Royo, Chromogenic detection of nerve agent mimics, Chem. Comm. (2008) 6002-4; A. M. Costero, M. Parra, S. Gil, R. Gotor, P. M. E. Mancini, R. Martinez-Manez, et al., Chromo-Fluorogenic Detection of Nerve-Agent Mimics Using Triggered Cyclization Reactions in Push-Pull Dyes, Chem.-Asian J. 5 (2010) 1573-1585. The effect of the electron-poor acceptor was also investigated by changing the substitution on that group. The synthesis of these dyes is shown in FIG. 4. As shown at 1 in FIG. 4, 2-(2-(Dimethylamino)phenyl)ethanol (1) was prepared by the method of Lupatelli and co-workers via a methylation of 2-(2-aminophenyl)ethanol using trimethyloxonium tetrafluoroborate in the presence of proton sponge. See also A. Solladie-Cavallo, P. Lupattelli, C. Bonini, V. Ostuni, and N. Di Blasio, New aniline-containing amino alcohols from trans-(R,R)-2-(2-nitrophenyl)-3-phenyloxirane as useful intermediates for the synthesis of chiral ligands, bases, and benzoxazine nucleus, J. Org. Chem. 71 (2006) 9891-9894. Reaction of 1 with the diazonium of 4-nitroaniline or 2-cyano-4-nitroaniline resulted in dyes 2 and 3 with peak absorptions at 417 and 480 nm respectively. A key feature of these dyes is the specific reactivity towards organophosphates, e.g., pesticides and chemical nerve agents.

Figure 5:
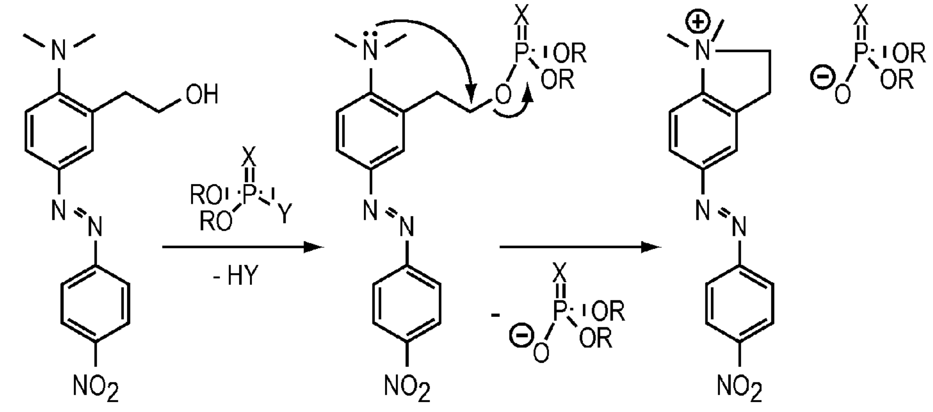
FIG. 5 illustrates activation chemistry of organophosphate detecting azobenzene dyes.

FIG. 5 illustrates the activation chemistry of the organophosphate detecting azobenzene dyes. The dye A contains a nucleophilic hydroxyl functional group capable of undergoing a acylation reaction with a phosphonate compound to form a covalently bound phosphate intermediate B. Due to the presence of the dimethylamino moiety, a rapid intramolecular N-alkylation takes place to afford the cyclized product C as a quarternary ammonium salt with a phosphate counter ion. In its unreacted form, dye A is an excellent push-pull dye with a strong absorption in the visible region. However, upon undergoing the cyclization reaction after reaction with an organophosphate to form C, the donor ability of the dimethylamino group is reduced, lowering the push-pull ability of the dye and resulting in a blue-shift of the dye absorption into the ultraviolet region, leaving them transparent in the visible.

Figure 6:
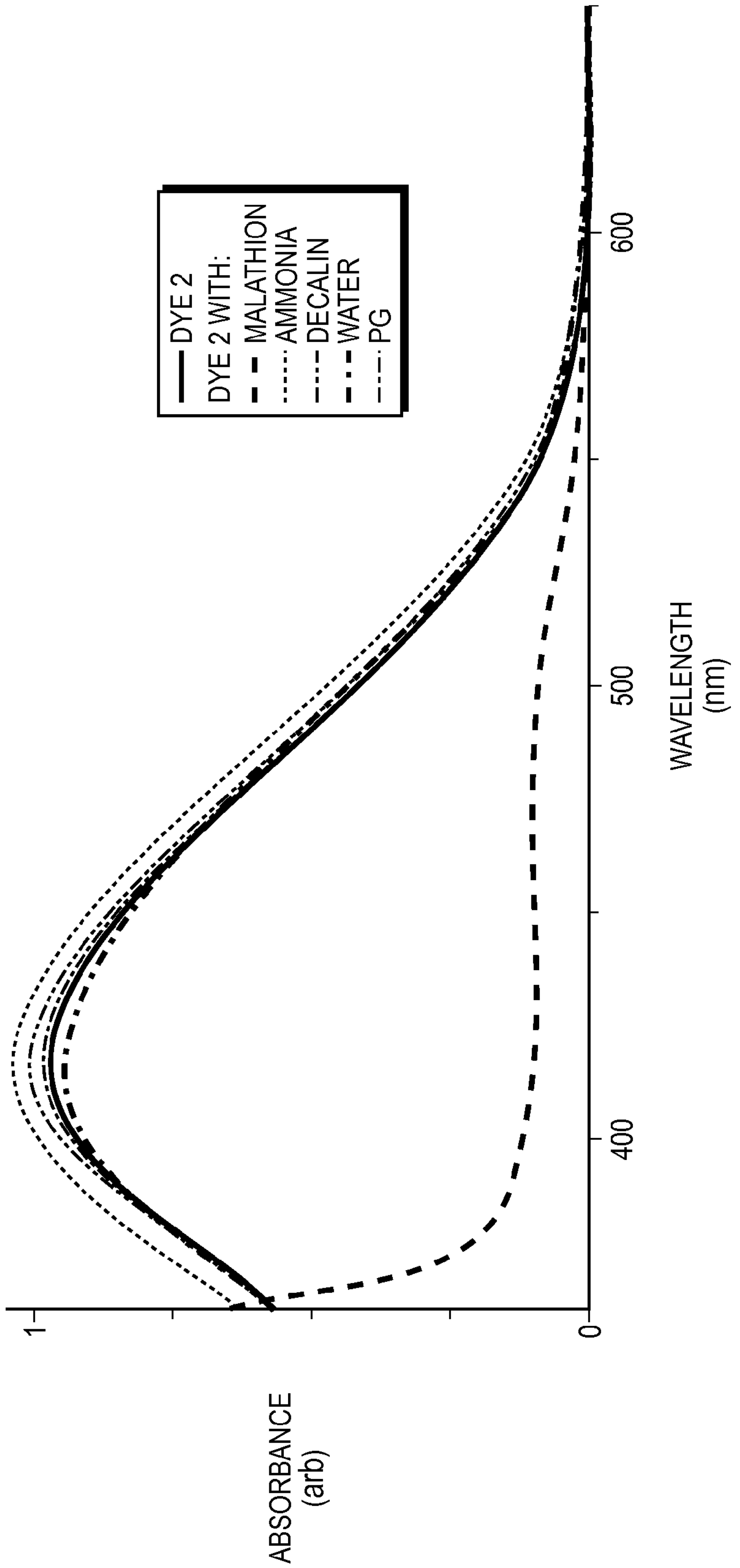
FIG. 6 illustrates absorbance of dye 2 of FIG. 4 in MeCN solution alone, in the presence of a surplus of target chemical malathion, and in the presence of several potential interferents: ammonia, decalin, water, and propylene glycol (PG). There is ~10:1 absorbance contrast at 417 nm with and without the target chemical, but essentially no response to the potential interferents.

FIG. 6 illustrates absorbance of dye 2 of FIG. 4 in MeCN solution alone, in the presence of a surplus of target chemical malathion, and in the presence of several potential interferents: ammonia, decalin, water, and propylene glycol (PG). As seen in FIG. 6, exposure of dye 2 to excess malathion in acetonitrile solution reduces the dye absorbance by 10-fold at 417 nm, while common contaminants such as water, ammonia, decalin, propylene glycol (PG) and so forth have essentially no effect. This outcome is also seen for both dyes 2 and 3 in polymer matrices on solid substrates as shown in FIG. 7.

Figure 7:
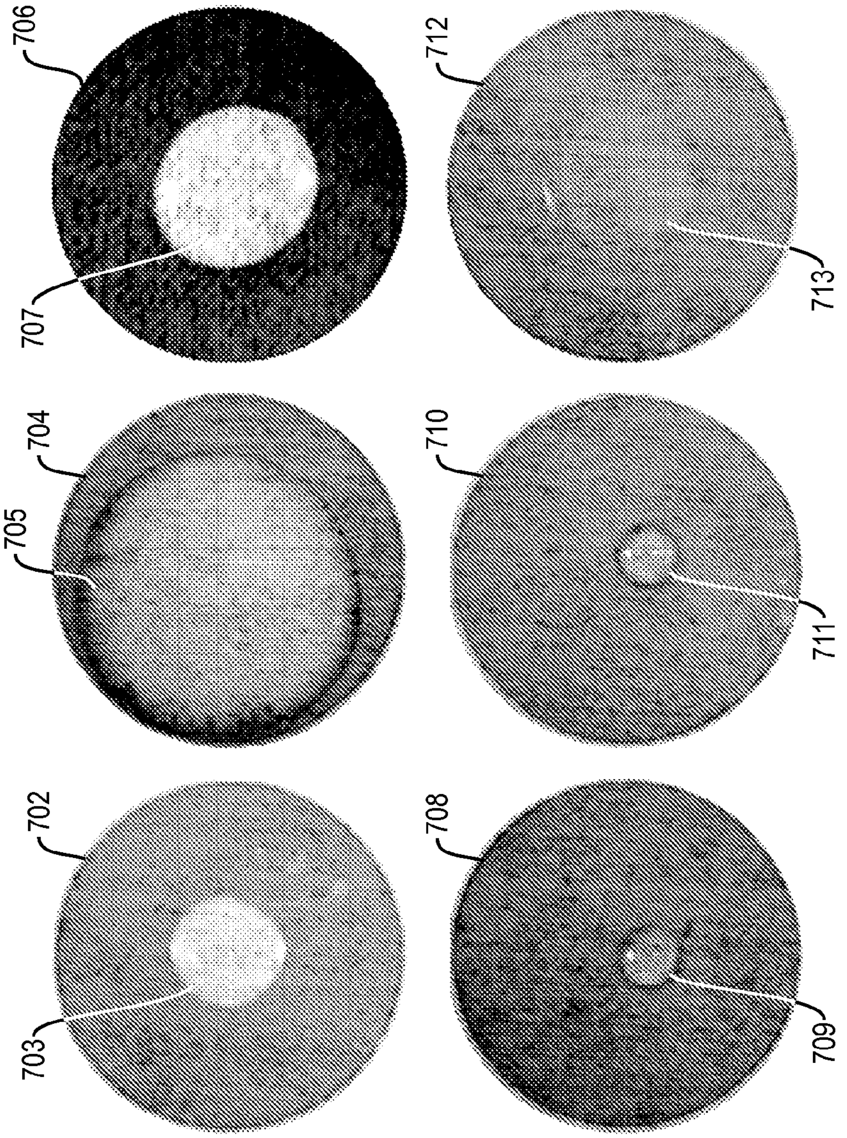
FIG. 7 illustrates samples of ~1 μm thick layers of 10% dye (dye 2 except as noted) in a polyester matrix on 25 mm diameter glass substrates. 10 μl drops of (clockwise from the top left) malathion, diethyl chlorophosphate (DCP), malathion (dye 3), decalin, 3% $H_2O_2$, and water have been applied to the samples. Only malathion and DCP (top row) cause a color change, e.g., bleaching of the dye.

FIG. 7 illustrates samples of ~1 μm thick layers of 10% dye (dye 2 except as noted) in a polyester matrix on 25 mm diameter glass substrates. A 10 μl drop of (clockwise from the top left) malathion, diethyl chlorophosphate (DCP), malathion (dye 3), decalin, 3% $H_2O_2$, and water has been applied to samples 702, 704, 706, 708, 710, and 712, respectively. Only malathion and DCP (top row of FIG. 7, samples 702, 704, 706) cause a color change. The color change is visible as a bleaching of the dye at regions 703, 705 and 707; whereas regions 709, 711, and 713 (i.e. those exposed to decalin, 3% $H_2O_2$, and water, respectively) show no color change. Beyond ~600 nm, the dye is transparent in both the contaminated and uncontaminated states, ensuring that targets can always be located by illuminating them in the red. In addition, measurement of the ratio of 417 nm to 600 nm reflectivity can be used to differentiate color change from changes in overall reflectance due, for example to dust accumulation on the retroreflectors.

Dye-Polymer System

For coating on the retroreflective surface, the dye can be mixed with a polymer. This polymer is an important component of the sensing system and preferably, should meet a number of criteria. First, it should provide an even, optically transparent coating on the retroreflector's protective top layer. It should also be durable in the sensing environment over the time required for a particular sensing application. In addition, the polymer itself should not react with the target chemical or likely contaminants. Finally, it should be permeable to the analyte to allow it to reach and react with the dye rapidly. As detailed above, the polymer can further enhance the sensing system by promoting the spreading of the target analyte, turning a small volume of contaminant into a large area of color change on the surface of the sensor.

Embodiments of the invention use a polyester, poly(1,4-butylene adipate), which fulfills many of these criteria. As seen in FIG. 7, a 1 μm thick polyester film with 10% dye spin-cast from cyclohexanone forms a suitable coating on a retroreflective target. These polyester films may provide long-term environmental stability of the sensor system, as such cast films on both glass and the retroreflector material show no evidence of degradation over months indoors or over 24 h of outdoor exposure on a sunny day.

Figure 8:
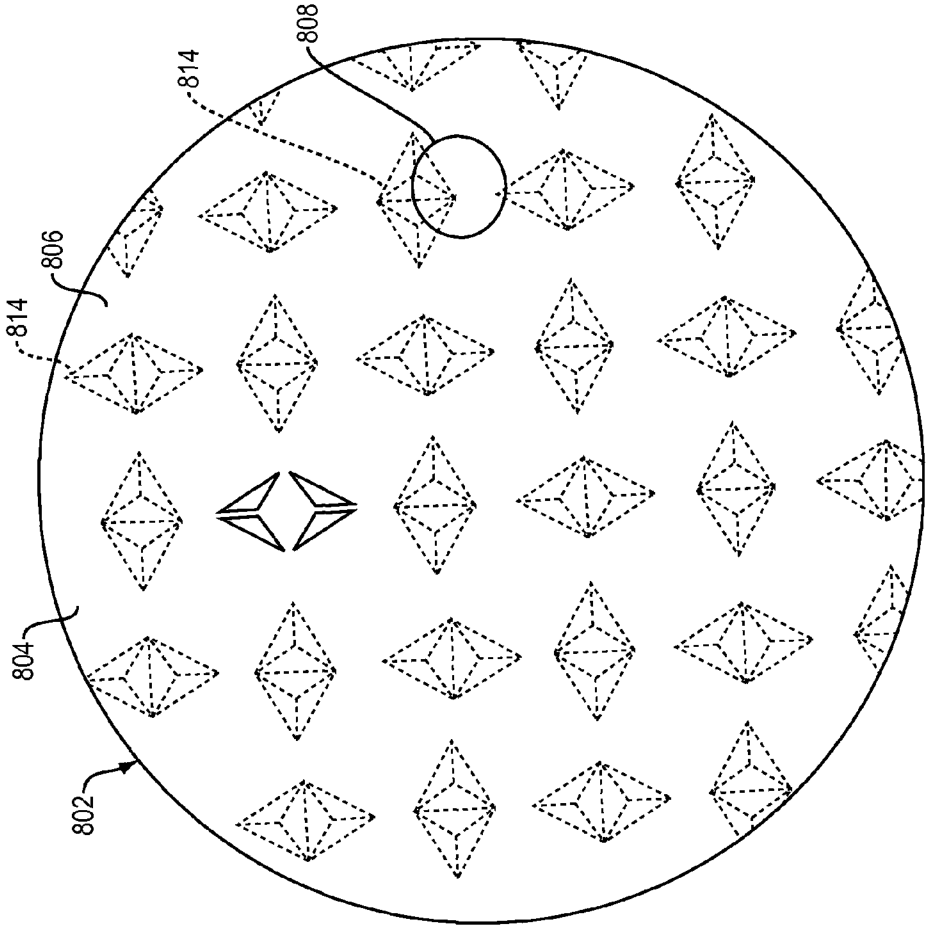
FIG. 8 illustrates a 25 cm diameter retroreflective target coated with ~1 μm of 10% dye 2 in poly(1,4-butylene adipate). A 100 nl drop of malathion applied at the 3 o'clock position changes the absorbance of the dye over a 3 mm diameter spot.

FIG. 8 illustrates a 25 cm diameter retroreflective target 802 coated with ~1 μm of 10% dye 2 in poly(1,4-butylene adipate) 804. In addition to long term environmental stability, such a coating can promote the spreading of the target analyte. As seen in FIG. 8, a 100 nl droplet of malathion deposited on this surface creates a ~3 mm diameter area 808 of color change ($\theta_c \approx 2°$), 5-fold larger than the diameter of a spherical droplet of the same volume. In this example, the retroreflective target 802 includes an array of prisms 814 of different orientations. Prisms 814 are visible through the colorimetric layer 804 in the area of color change 808 and in the area where the dye remained in its native state, e.g., at 806.

Optical Illuminator/Receiver

Figure 9:
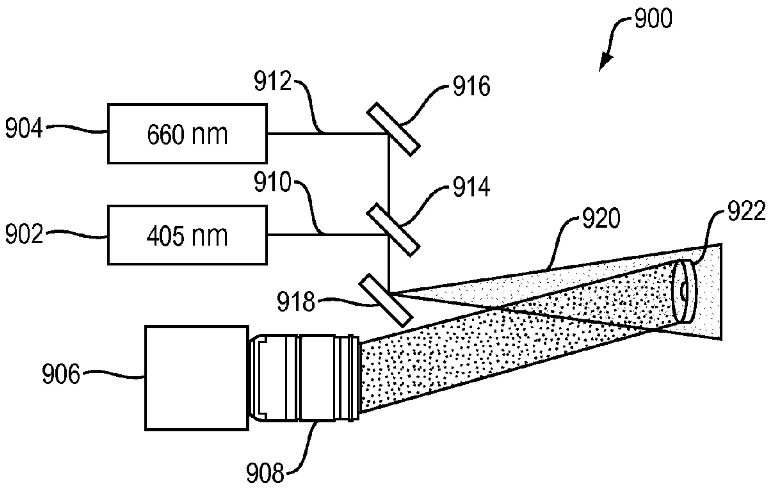
FIG. 9 is a schematic illustration of an optical illuminator/receiver system including two low-power diode lasers and a camera for remote detection using retroreflectors.

A component of the sensing system is the illuminator/receiver, an example of which is illustrated in FIG. 9. A prototype illuminator/receiver system as shown was constructed from commercial off-the-shelf parts. The exemplary illuminator/receiver includes two laser diodes 902 and 904, one at 405 nm and one at 660 nm (Coherent Inc., Santa Clara, Calif.) along with a CCD camera 906 (Princeton Instruments, Trenton, N.J.) and an inexpensive catadioptric lens 908 (500 mm f/8, Tamron Inc., Saitama, Japan). Lasers 902 and 904 emit laser beams 910 and 912 which are directed by mirrors 914 and 916. The laser beams are reflected from a final mirror 918 mounted on a galvanometer motor (not shown) which sweeps 920 the beams over the area to be illuminated, including retroreflective target 922, at several hundred Hz, decreasing the coherence of the illumination and preventing speckle.

Preferably, the reflected light will be measured at two or more wavelengths whose reflectivity is affected differently by the color change allowing other causes of reflectivity change (e.g. dust on the substrate) to be excluded. In the illuminator/receiver system shown in FIG. 9, two lasers 902 and 904 having different wavelengths illuminate the retroreflector 922. The illumination with different wavelengths may occur at different times, such that camera 906 can detect the signal (reflectivity) at a particular wavelength. The illuminator/receiver system 900 may also include one or more filters (e.g., at camera 906 or lens 908, or at the light source in the case of a white light illuminator) to select retroreflected wavelengths for measurement, in which case illumination with different wavelengths can occur simultaneously. For example, to measure at two or more wavelengths, the retroreflective element 922 may be illuminated with radiation from a white light source (instead of lasers 902 and 904) and camera 906 may sense the retroreflected radiation using filtering at different retroreflected wavelengths, including the filtering built into standard digital color cameras.

Figure 10A:
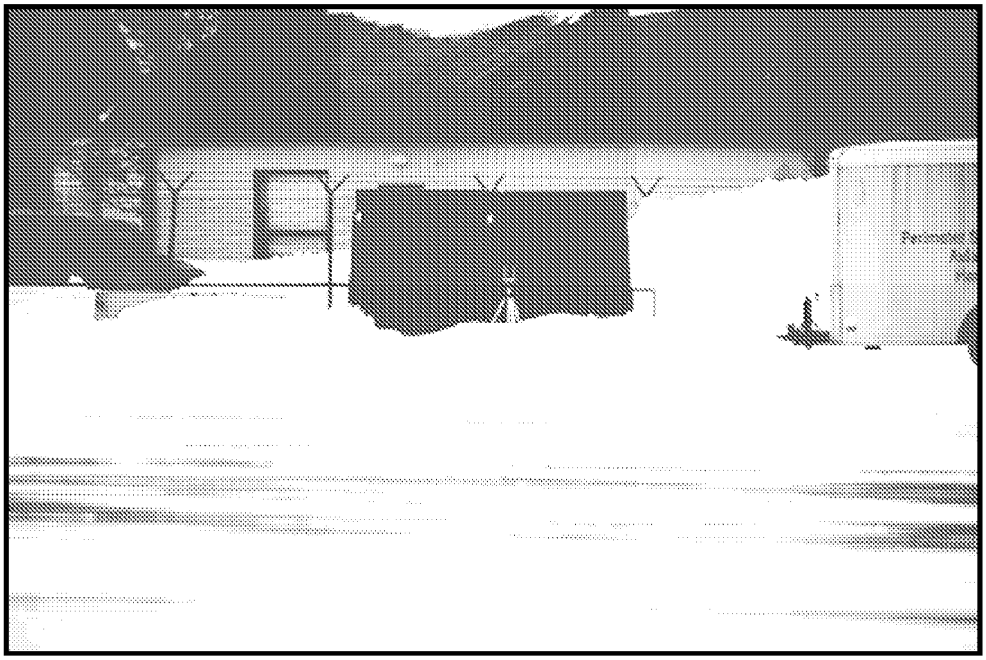
FIGS. 10A-E show images of a 25 mm diameter dye coated retroreflector target at 150 m. A 1 μl droplet of malathion has been placed on the left side of the target. The entire camera field of view is shown in FIG. 10A. Insets: the target with (FIG. 10B) only ambient illumination, (FIG. 10C) 660 nm laser illumination, (FIG. 10D) 405 nm illumination, and (FIG. 10E) the ratio of light reflected at 405 nm to that reflected at 660 nm.
Figure 10B:
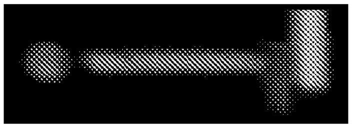
Figure 10C:
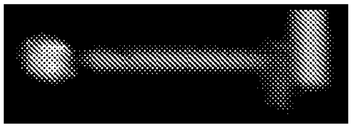
Figure 10D:
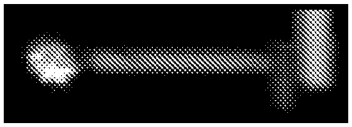
Figure 10E:
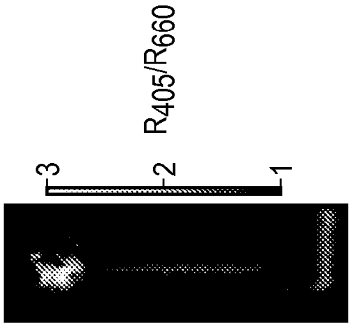

The prototype illuminator/receiver system 900 described above can, for example, detect a 1 μl droplet of malathion on a retroreflective target at the a distance of 150 m, outdoors in sunlight. FIG. 10A shows the entire field of view of the camera at this range, with no laser illumination. Inset are close-up images of the contaminated target with no laser illumination (FIG. 10B), 1 mW of laser power at 660 nm (FIG. 10C), and 18 mW at 405 nm (FIG. 10D). At 660 nm, the entire target lights up, while at 405 nm, only the left, contaminated portion does. This contaminated area has almost three times the signal at 405 as at 660 nm, while for the uncontaminated portion of the same retroreflector has only half (FIG. 10E).

With the present approach, wavelength selection may be accomplished at the radiation source or at the sensor, or both, which can mitigate the effect of stray light from the environment. In one possible mode, the retroreflector is illuminated with white light and a wavelength dependent sensor is used to sense the reflected light. The wavelength dependent sensor may use filters to sense reflected light at selected wavelengths. In another possible mode, the retroreflective element is illuminated using one or more specific wavelength light sources, e.g., two lasers as shown in FIG. 9, in which case one can detect a broad spectrum of light with the sensor.

Figure 11:
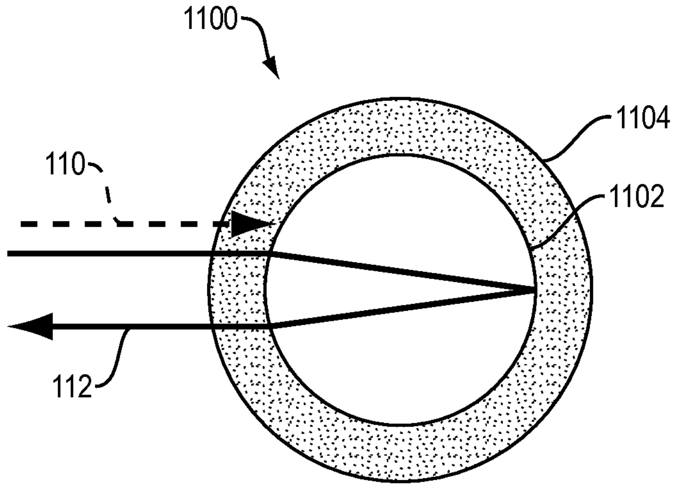
FIG. 11 illustrates an embodiment of a retroreflective device that includes a cat's eye retroreflector.

FIG. 11 illustrates another embodiment of a retroreflective element according to the present approach. Retroreflective element 1100 includes a cat's eye retroreflector 1102 coated with a layer of material 1104 that changes transmission with respect to an optical property of radiation when exposed to a phenomenon to be sensed. Similar to layer 104 of device 100 (FIG. 1A), the layer of material 1104 may be subject to change in, among others, color, polarization, optical chirality, or non-linear properties. Retroreflective element 1100 may be remotely interrogated by illuminating element 1100 using a radiation source of multiple aspects of the optical property, e.g., multiple wavelengths, multiple states of polarization, or multiple intensities, and sensing radiation reflected through layer 1104. For example, the layer 1104 of element 1100 can include a colorimetric dye, such as the azobenzene dyes described herein. In its native state, the colorimetric dye absorbs one wavelength of light 110 and allows another wavelength of light 112 to pass. The wavelength of light 112 that is allowed to pass is reflected back to the source by the cat's eye retroreflector 1102. A sensor collocated with the source can be used to detect any retroreflected wavelengths. When activated by a phenomenon to be sensed, the dye in the colorimetric layer 1104 allows both wavelengths to pass and both wavelengths are retroreflected. As described elsewhere herein, the phenomenon to be sensed can include any combination of temperature, pH, and the presence or absence of a chemical.

As shown in FIG. 11, the cat's eye retroreflector 1102 of element 1100 can be a microsphere. In one embodiment, retroreflector 1102 is a microball about 0.5 to 1 mm in size. Retroreflector 1102 may be a glass microsphere and preferably has a high index of refraction. Advantageously, element 1100 can retroreflect light from any direction. Element 1100 can be a projectile or attached to a projectile or other suitable carrier, which may be thrown or shot into an area of suspected contamination. Microsphere reflective elements 1100 are particularly suitable to be distributed into an area and interrogated remotely.

Described herein are a new indicator dye specific to organophosphate contaminants and an inexpensive retroreflector-based system to read out that dye remotely. Performance modeling indicates that such a system can be used at kilometer ranges for small droplets of contamination. Such a system may be used for hazardous chemical detection at fixed sites. For example, the United States Air Force currently relies on a colorimetric paper placed on a grid of stands to detect and map the extent of a suspected chemical attack on an airbase. See Air Force Manual 10-2602 Nuclear, Biological, Chemical, and Conventional (NBCC) Defense Operations and Standards Review, United States Air Force, 2003. Reading out such a system post attack requires trained personnel to visit each stand with the attendant risks and requirements for personal protective equipment and provisions for decontamination. It is also slow. In contrast, a retroreflector-based system with the same grid layout can eliminate the risk to personnel, and measure the same contamination in a fraction of the time.

Figure 12A:
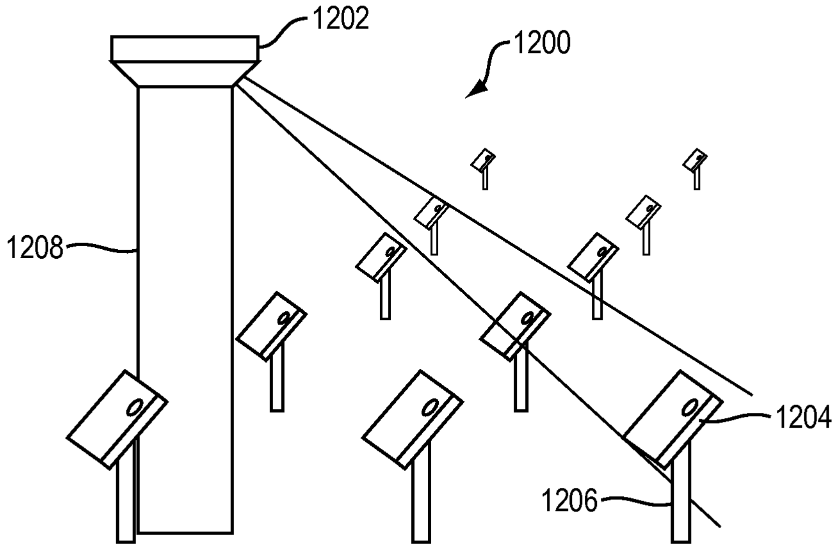
FIG. 12A illustrates a retroreflector-based system that includes an illuminator/receiver for remotely interrogating fixed retroreflective elements.

FIG. 12A illustrates a retroreflector-based system 1200 that includes an illuminator/receiver 1202 for remotely interrogating fixed retroreflective elements 1204. Each element 1204 may be mounted on a stand 1206 and positioned to face illuminator/receiver 1202, which preferably is located at an elevated position, e.g., at the top of a tower 1208. For example, illuminator/receiver 1202 may include system 900 described above, which may be modified for use with multiple retroreflectors 1204 distributed over a region. Each retroreflective element 1204 can include a colorimetric dye that is read out remotely by illuminator/receiver 1202 using radiation of multiple wavelengths as described herein. For example, illuminator/receiver 1202 can interrogate each of elements 1204 in the same manner system 900 reads out element 922 (FIG. 9). Any retroreflective devices described herein, such as retroreflective elements 100 and 1100, may be used in system 900.

Figure 12B:
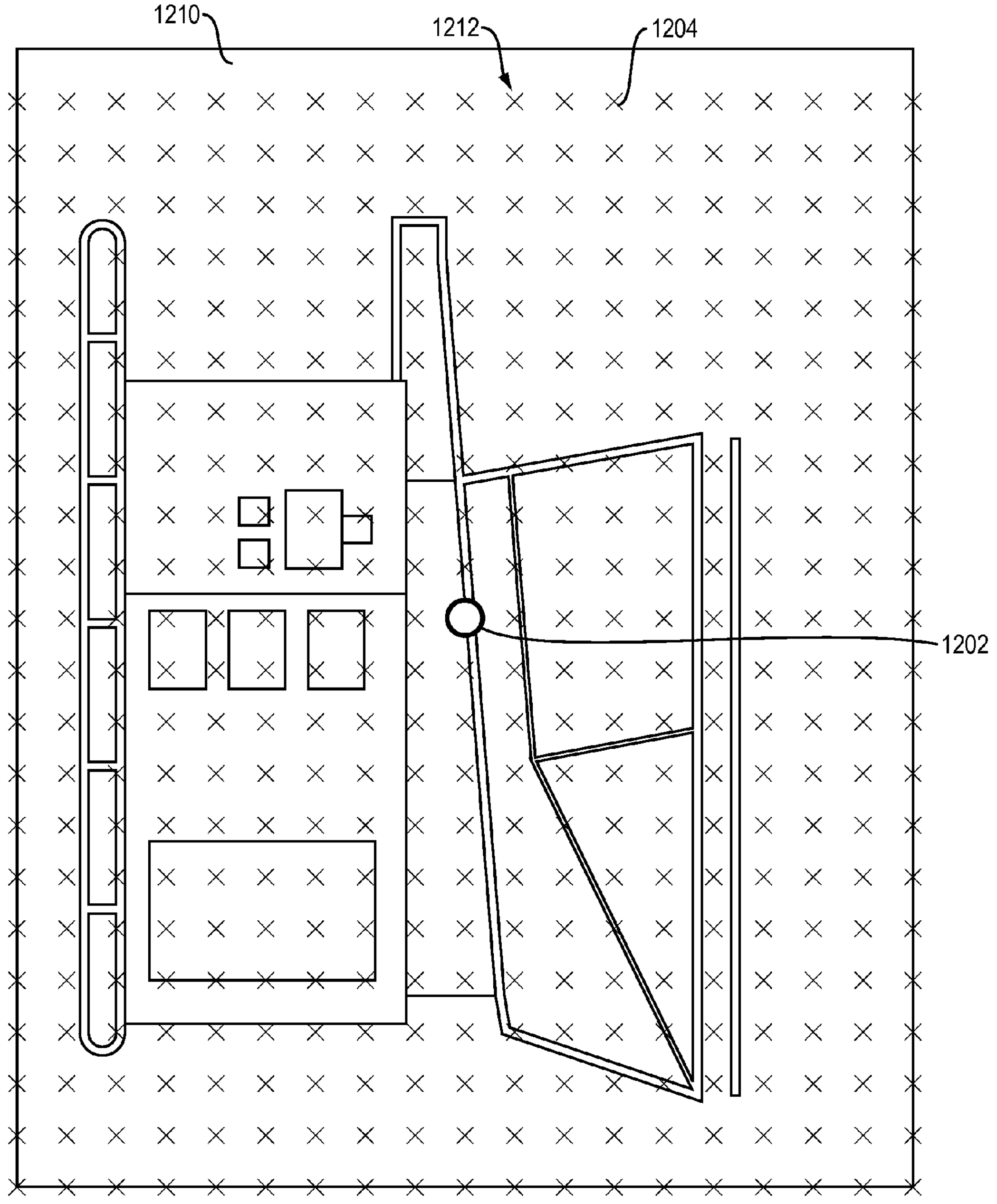
FIG. 12B schematically illustrates possible deployment of the retroreflector-based system of FIG. 12A at an airfield.

FIG. 12B illustrates as possible deployment of the retroreflector-based system 1200 of FIG. 12A. As shown, the illuminator/receiver 1202 is fixed in the center of an airfield 1210. An array of unconnected retroreflective elements 1204 is arranged in a grid 1212, each retroreflective element indicated as an X. For example, retroreflectors may be located on a grid of 250 m spacing. As shown, 437 retroreflective devices 1204 may be spaced on a grid to cover an area of 4,500 m×5,500 m.

As in conventional hazardous chemical detection, applications of pesticides is often monitored with cards whose read-out, while not posing the same risks, is still time consuming and thus expensive. Pre-positioned retroreflectors, such as those shown in FIGS. 12A-B, can be read-out from the air quickly over a wide area, potentially by the same aircraft applying the pesticide. Other applications where retroreflectors according to embodiments of the invention might be useful include monitoring water quality, e.g. temperature, salinity, pH, or contamination with a particular chemical, either over a wide area or in remote locations where manual readout would be difficult. Retroreflective targets, coated with one or more appropriate dyes, can be designed to float just under the surface of the water and be read out either from shore or from the air.

Figure 13A:
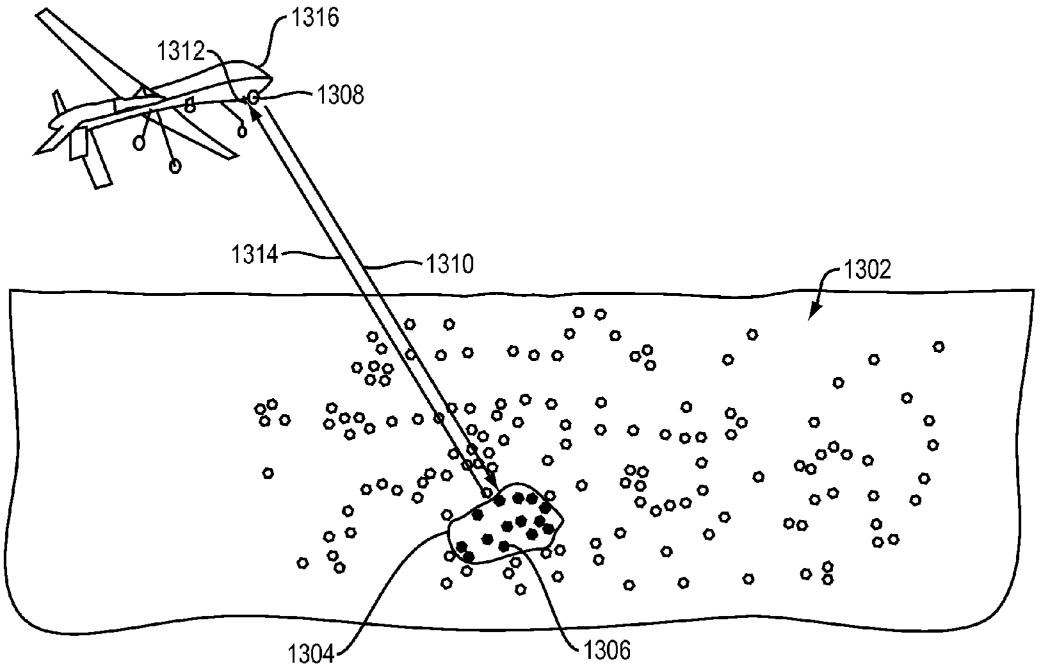
FIGS. 13A and 13B illustrate detection systems including retroreflective elements that are distributed into an area of suspected contamination and interrogated remotely.
Figure 13B:
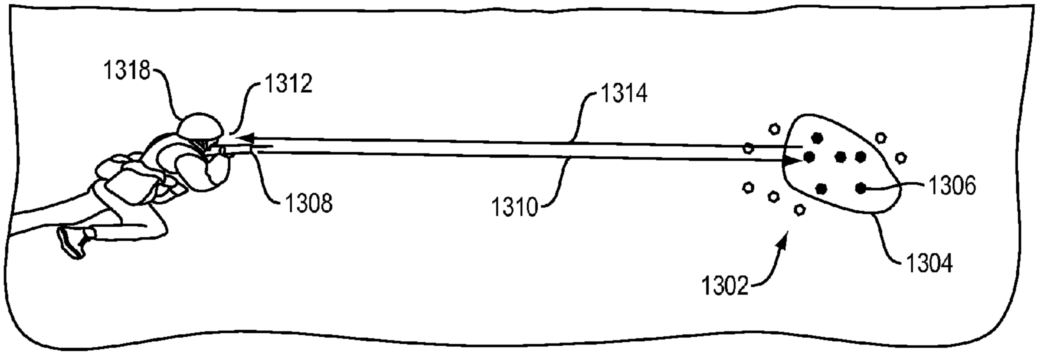

Retroreflectors according to embodiments of the invention may also be useful in mapping contamination which has already occurred. As illustrated in FIGS. 13A and 13B, unconnected retroreflective targets or elements 1302, each including a colorimetric dye, may be thrown, dropped, shot or otherwise distributed into an area of suspected contamination and interrogated remotely. Retroreflective targets 1302 may be small and may be distributed in an array. The area 1304 over which the indicator dye changes color 1306 would indicate the extent of the contamination, facilitating isolation and eventual cleanup efforts. As illustrated in FIG. 13A, the retroreflective elements 1302 may be interrogated from the air, e.g., from an aircraft 1316 that includes a radiation source 1308 to illuminate 1310 the retroreflective elements 1302 and a sensor 1312 sensing radiation reflected 1314 from the retroreflective elements 1302. As illustrated in FIG. 13B, the retroreflective elements 1302 may be interrogated from the ground, for example, from a person using a wearable detection system 1318 that includes a radiation source 1308 to illuminate 1310 the retroreflective elements 1302 and a sensor 1312 sensing radiation reflected 1314 from the retroreflective elements.

The retroreflective elements 1302 of FIGS. 13A and 13B may be small projectiles. In one embodiment, each retroreflective element includes a retroreflector and a colorimetric layer attached to the surface of a small projectile or other carrier, which is thrown, dropped, shot or otherwise introduced into an area of suspected contamination and interrogated remotely. A large number of such small projectiles could also be dispersed into an aerosol and interrogated while in the air to detect the nature of the aerosol. In these cases, the efficiency of the retroreflector-covered projectiles allows a very high sampling efficiency by covering the entire zone of interest in detectors. Instead of a colorimetric dye, retroreflective elements 1302 can include a material that changes in polarization, optical chirality, or non-linear properties (e.g., variation of transmission with light intensity) with exposure to the contaminant or other phenomenon.

Embodiments for retroreflector-based remote sensing may use specific indicator dyes developed or adapted for each sensing target. For droplet sensing applications, maximum analyte spreading is desirable, so an appropriate polymer system or other means of promoting analyte spreading may be used. For many applications, weather resistance is desirable, and the dyes and polymers may be selected for their environmental stability. For kilometer range performance beyond the 150 m demonstrated in FIG. 10, illumination and optics of the retroreflector system may be adjusted appropriately. Further, a detection system that includes plural retroreflective elements distributed over a region can be used for post-contamination mapping with retroreflector coated targets, e.g., plural retroreflective elements 1100.

The retroreflective sensors described herein need not be limited to hazardous chemical detection. For example, a retroreflector with a pH or temperature sensitive layer attached to a buoy could be used to monitor the condition of a body of water. Because of their retroreflective nature, sensors spread out over many kilometers could be monitored from a single station (see FIGS. 12A-B) or from an aircraft flying overhead (see FIG. 13A). A wide variety of remote industrial and environmental monitoring (the spread of pesticides, chemical or heat leaks, etc.) are also possible.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A detection system comprising:

an array of physically unconnected retroreflective elements distributed over a region to map across the array the presence or absence of a chemical in an environment, each retroreflective element including a material having a chemical composition that changes its chemistry when exposed to the chemical in the environment, the material being subject to a change in light absorption of the material, on exposure to the chemical, that results in a change in transmission of incident radiation through the material having the chemical composition, the retroreflective element being able to retroreflect light from any direction and being exposed to light in all directions;

a radiation source to illuminate the retroreflective elements with radiation at multiple values of an optical property of the radiation; and a sensor sensing radiation reflected from the retroreflective elements.

2. The detection system of claim 1 wherein the retroreflective elements are projectiles distributed into an aerosol and through the atmosphere.

3. The detection system of claim 1 wherein the retroreflective elements are arranged in a grid across a region of ground.

4. The detection system of claim 1 wherein each retroreflective element comprises a prism.

5. The detection system of claim 1 wherein each retroreflective element comprises a cat's eye microsphere.

6. The detection system of claim 1 wherein the retroreflective elements have a varied response in retroreflected wavelength on exposure to the chemical.

7. The detection system of claim 1 wherein the radiation source illuminates a region of each retroreflective element with radiation at multiple values of the optical property, and wherein the sensor senses radiation being retroreflected from the region.

8. The detection system of claim 1 wherein each retroreflective element is a single cat's eye retroreflector coated with a layer of the material, the retroreflector being a ball that is completely surrounded by the layer of the material, the retroreflector and layer being exposed to light in all directions.

9. The detection system of claim 1 wherein the material is subject to color change on exposure to the chemical and the radiation source emits radiation at multiple wavelengths.

10. The detection system of claim 9 wherein the radiation source comprises plural lasers of different wavelengths.

11. The detection system of claim 9 wherein the sensor comprises plural filters for different wavelengths.

12. The detection system of claim 9 wherein the material comprises a colorimetric dye.

13. A method of detecting a chemical comprising:

distributing an array of physically unconnected retroreflective elements over a region to map across the array the presence or absence of a chemical in an environment, each retroreflective element including a material having a chemical composition that changes its chemistry when exposed to the chemical in the environment, the material being subject to a change in light absorption of the material, on exposure to the chemical, that results in a change in transmission of incident radiation through the material having the chemical composition;

illuminating the array of retroreflective elements with radiation at multiple values of an optical property of the radiation; and sensing radiation retroreflected from the retroreflective elements.

14. The method of claim 13 wherein the retroreflective elements are illuminated with multiple wavelengths and wherein sensing radiation comprises filtering at different retroreflected wavelengths.

15. The method of claim 13 wherein the retroreflective elements are illuminated with different wavelengths at different times.

16. The method of claim 13 wherein a region of each retroreflective element is illuminated with radiation at multiple values of the optical property, and wherein radiation retroreflected from the region is sensed.

17. The method of claim 13 wherein each retroreflective element is a single cat's eye retroreflector coated with a layer of the material, the retroreflector being a ball that is completely surrounded by the layer of the material, the retroreflector and layer being exposed to light in all directions.

18. The method of claim 13 wherein the retroreflective elements are illuminated with radiation at multiple wavelengths and the material is subject to color change on exposure to the chemical.

19. The method of claim 18 wherein retroreflective elements are illuminated with lasers.

20. A detection device consisting of a single cat's eye retroreflector coated with a layer of material, the material having a chemical composition that changes its chemistry when exposed to a chemical in an environment, the material changing transmission of incident radiation through the material as a result of a change in an intrinsic optical property of the material when exposed to the chemical, the retroreflector being a ball that is completely surrounded by the layer of material and that can retroreflect light from any direction, the retroreflector and layer being exposed to light in all directions.

21. The retroreflector of claim 20 wherein the retroreflector is a microsphere.

22. The retroreflector of claim 20 wherein the material comprises a colorimetric dye.

23. A detection device comprising:

an array of physically unconnected retroreflective elements distributed over a region to map across the array the presence or absence of a chemical in an environment, each retroreflective element including:

a retroreflector that can retroreflect light from any direction; and a layer of material over the retroreflector, the material having a chemical composition that changes its chemistry when exposed to the chemical in the environment, the material being subject to a change in light absorption of the material, on exposure to the chemical, that results in a change in transmission of incident radiation through the material having the chemical composition, the retroreflector and layer being exposed to light in all directions.

24. The detection device of claim 23 wherein the retroreflector and layer comprise a projectile.

25. The detection device of claim 23 wherein the retroreflector comprises a cat's eye microsphere.

26. The detection device of claim 23 further comprising a radiation source emitting radiation at multiple values of the optical property to illuminate the retroreflector through the layer and a sensor sensing radiation passing through the layer and subsequently being retroreflected.

27. The detection system of claim 26 wherein the radiation source illuminates a region of the retroreflector with radiation at multiple values of the optical property, and wherein the sensor senses radiation being retroreflected from the region.

* * * * *